United States Patent [19]

Chang et al.

[11] Patent Number: 5,563,311

[45] Date of Patent: *Oct. 8, 1996

[54] PROCESS FOR PREPARING SHORT CHAIN ALKYL AROMATIC COMPOUNDS

[75] Inventors: Clarence D. Chang, Princeton; Jane C. Cheng, Clarksburg; Scott Han, Lawrenceville, all of N.J.; José G. Santiesteban, Yardley; Dennis E. Walsh, Richboro, both of Pa.

[73] Assignee: Mobil Oil Corporation, Fairfax, Va.

[ * ] Notice: The term of this patent shall not extend beyond the expiration date of Pat. No. 5,516,954.

[21] Appl. No.: 365,335

[22] Filed: Dec. 28, 1994

Related U.S. Application Data

[63] Continuation of Ser. No. 120,493, Sep. 4, 1993, abandoned.

[51] Int. Cl.[6] .................................. C07C 2/00; C07C 5/52
[52] U.S. Cl. ........................ 585/467; 585/446; 585/470; 585/471
[58] Field of Search .................................. 585/446, 463, 585/467, 470, 471

[56] References Cited

U.S. PATENT DOCUMENTS

| | | | |
|---|---|---|---|
| 3,153,677 | 10/1964 | Domash et al. | 585/467 |
| 3,692,696 | 9/1972 | Kravitz et al. | 252/439 |
| 3,751,504 | 8/1973 | Keown et al. | 260/672 T |
| 4,259,537 | 3/1981 | Chu | 585/467 |
| 4,459,426 | 7/1984 | Inwood et al. | 585/323 |
| 4,891,458 | 1/1990 | Innes et al. | 585/323 |
| 4,992,606 | 2/1991 | Kushnerick et al. | 585/467 |
| 5,113,034 | 5/1992 | Soled et al. | 585/510 |
| 5,396,011 | 3/1995 | Kuhn | 585/455 |

FOREIGN PATENT DOCUMENTS 1-288339  11/1989  Japan .

OTHER PUBLICATIONS

Hino, M. et al., "Synthesis of Solid Superacid of Tungsten Oxide supported on Zirconia and its Catalytic Action for Reactions of Butane and Pentane," J. Chem. Soc. Chem. Comm., 1259–1260 (1988).

European Publication No. WO94/14732 (1994).

Proceedings 9th International Congress on Catalysis, vol. 4, M. J. Phillips, et al. (ed.), Oxide Catalysts and Catalyst Development, 1727–1734 (1988).

*Primary Examiner*—Ponnathapura Achutamurthy
*Attorney, Agent, or Firm*—Ronald A. Bleeker; Dennis P. Santini; Lori F. Cuomo

[57] ABSTRACT

Relatively short chain alkyl aromatic compounds are prepared by alkylating or transalkylating an alkylatable aromatic compound with a relatively short chain alkylating or transalkylating agent under sufficient reaction conditions in the presence of catalyst comprising an acidic solid material which comprises a Group IVB metal oxide, such as zirconia, modified with an oxyanion of a Group VIB metal, such as tungsten.

14 Claims, No Drawings

PROCESS FOR PREPARING SHORT CHAIN ALKYL AROMATIC COMPOUNDS

This is continuation of application Ser. No. 08/120,493, filed Sep. 4, 1993, now abandoned.

BACKGROUND

There is provided a process for preparing short chain alkyl aromatic compounds by alkylating or transalkylating an aromatic compound with an alkylating or transalkylating agent employing a particular acidic solid material as a catalyst. This acidic solid comprises a Group IVB metal oxide, such as zirconia, modified with an oxyanion of a Group VIB metal, such as tungstate.

The alkylation of aromatic hydrocarbons with an olefin in the presence of a zeolite having uniform pore openings of from about 6 to about 15 Angstrom units is described in U.S. Pat. No. 2,904,607. U.S. Pat. No. 3,251,897 describes the liquid phase alkylation of aromatic hydrocarbons in the presence of X- or Y-type zeolites, specifically such zeolites wherein the cation is a rare earth metal species and/or hydrogen. U.S. Pat. Nos. 3,751,504 and 3,751,506 describe the vapor phase alkylation of aromatic hydrocarbons with olefins, e.g., benzene with ethylene, in the presence of catalyst comprising, for example, ZSM-5.

U.S. Pat. Nos. 3,631,120 and 3,641,177, describe a liquid phase process for the alkylation of aromatic hydrocarbons with olefins in the presence of certain zeolites.

U.S. Pat. Nos. 4,962,256; 4,992,606; 4,954,663; 5,001,295; and 5,043,501, each incorporated herein by reference in its entirety, teach alkylation of aromatic compounds with various alkylating agents over catalyst comprising a particular crystalline material, such as PSH-3 or MCM-22. U.S. Pat. No. 4,962,256 describes preparing long chain alkylaromatic compounds by alkylating an aromatic compound with a long chain alkylating agent. U.S. Pat. No. 4,992,606 describes preparing short chain alkylaromatics by alkylating an aromatic compound with a short chain alkylating agent. U.S. Pat. No. 4,954,663 teaches alkylation of phenols, and U.S. Pat. No. 5,001,295 teaches alkylation of naphthalene. U.S. Pat. No. 5,043,501 describes preparation of 2,6-dimethylnaphthalene.

U.S. Pat. Nos. 3,755,483 and 4,393,262 disclose the vapor phase reaction of propylene with benzene in the presence of zeolite ZSM-12, to product isopropylbenzene.

U.S. Pat. No. 4,469,908 discloses the alkylation of aromatic hydrocarbons with relatively short chain alkylating agents having from 1 to 5 carbon atoms employing ZSM-12 as alkylation catalyst.

Harper et al. have described a catalytic alkylation of benzene with propylene over a crystalline zeolite (*Petrochemical Preprints,* American Chemical Society, vol. 22, no. 3, 1084 (1977)). Extensive kinetic and catalyst aging studies were conducted with a rare earth exchanged Y-type zeolite (REY) catalyst.

Ethylbenzene is a valuable commodity chemical which is currently used on a large scale industrially for the production of styrene monomer. Ethylbenzene may be produced by a number of different chemical processes but one process which has achieved a significant degree of commercial success is the vapor phase alkylation of benzene with ethylene in the presence of a solid, acidic ZSM-5 zeolite catalyst. In the production of ethylbenzene by this process, ethylene is used as the alkylating agent and is reacted with benzene in the presence of the catalyst at temperatures which vary between the critical temperature of benzene up to 900° F. (about 480° C.) at the reactor inlet. The reactor bed temperature may be as much as 150° F. (about 85° C.) above the reactor inlet temperature and typical temperatures for the benzene/ethylene reaction vary from 600° to 900° F. (315° to 480° C.), but are usually maintained above about 700° F.(about 370° C.) in order to keep the content of the more highly alkylated benzenes such as diethylbenzene at an acceptably low level. Pressures typically vary from atmospheric to 3000 psig (about 20785 kPa abs) with a molar ratio of benzene to ethylene from about 1:1 to 25:1, usually about 5:1 (benzene:ethylene). Space velocity in the reaction is high, usually in the range of 1 to 6, typically 2 to 5, WHSV based on the ethylene flow, with the benzene space velocity varying accordingly, in proportion to the ratio of the reactants. The products of the reaction include ethylbenzene which is obtained in increasing proportions as temperature increases together with various polyethylbenzenes, principally diethylbenzene (DIEB) which also are produced in increasing amounts as reaction temperature increases. Under favorable operating conditions on the industrial scale, an ethylene conversion in excess of 99.8 weight percent may be obtained at the start of the cycle.

In a commercial operation of this process, the polyalkylated benzenes, including both polymethylated and polyethylated benzenes are recycled to the alkylation reactor in which the reaction between the benzene and the ethylene takes place. By recycling the by-products to the alkylation reaction, increased conversion is obtained as the polyethylated benzenes (PEB) are converted to ethylbenzene (EB). In addition, the presence of the PEB during the alkylation reaction reduces formation of these species through equilibration of the components because at a given feed composition and under specific operating conditions, the PEB recycle will reach equilibrium at a certain level. This commercial process is known as the Mobil/Badger process and is described in more detail in an article by Francis G. Dwyer, entitled "Mobil/Badger Ethylbenzene Process-Chemistry and Catalytic Implications", appearing on pages 39–50 of a book entitled *Catalysis of Organic Reactions,* William R. Moser, ed., Marcel Dekker, Inc. (1981).

Ethylbenzene production processes are described in U.S. Pat. Nos. 3,751,504 (Keown); 4,547,605 (Kresge); and 4,016,218 (Haag); reference is made to these patents for a detailed description of such processes. The process described in U.S. Pat. No. 3,751,504 is of particular note since it includes a separate transalkylation step in the recycle loop which is effective for converting a significant proportion of the more highly alkylated products to the desired ethylbenzene product. Other processes for the production of ethylbenzene are disclosed in U.S. Pat. Nos. 4,169,11 (Wight) and 4,459,426 (Inwood), in both of which a preference for large pore size zeolites such as zeolite Y is expressed, in distinction to the intermediate pore size zeolites used in the processes described in the Keown, Kresge, and Haag patents. U.S. Pat. No. 3,755,483 (Burress) describes a process for the production of ethylbenzene using zeolite ZSM-12 as the alkylation catalyst.

Ethylbenzene (EB) can be synthesized from benzene and ethylene ($C_2=$) over a variety of zeolitic catalysts in either the liquid phase or in the vapor phase. An advantage of a liquid phase process is its low operating temperature and the resulting low content of by-products.

U.S. Pat. No. 4,891,458 describes the liquid phase synthesis of ethylbenzene and cumene with zeolite beta.

U.S. Pat. No. 5,149,894 describes the liquid phase synthesis of ethylbenzene and cumene with a crystalline aluminosilicate material designated SSZ-25.

SUMMARY

There is provided a process for preparing short chain alkyl aromatic compounds, said process comprising contacting at least one alkylatable aromatic compound with at least one alkylating or transalkylating agent possessing an alkylating aliphatic group having from 1 to 5 carbon atoms under sufficient reaction conditions and in the presence of a catalyst to provide an alkylated aromatic product possessing at least one alkyl group derived from said alkylating or transalkylating agent, said catalyst comprising an acidic solid comprising a Group IVB metal oxide, such as zirconia, modified with an oxyanion of a Group VIB metal.

There is also provided a process for the production of ethylbenzene, said process comprising alkylating benzene with ethylene under sufficient liquid phase conditions in the presence of a catalyst comprising an acidic solid comprising a Group IVB metal oxide, such as zirconia, modified with an oxyanion of a Group VIB metal.

EMBODIMENTS

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a hetero atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene.

Generally the alkyl groups which can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as those produced by the alkylation of aromatic hydrocarbons with olefin oligomers. Such product are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes make in such instances may be less than about 500 ppm.

Reformate containing substantial quantities of benzene, toluene and/or xylene constitutes a particularly useful feed for the alkylation or transalkylation process of this invention.

The alkylating agents which are useful in the process of this invention generally include any aliphatic or aromatic organic compound having one or more available alkylating aliphatic groups capable of reaction with the alkylatable aromatic compound, the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refenery FCC propane/propylene streams, etc., are useful alkylating agents herein. For example, a typical FCC light olefin stream possesses the following composition:

|  | Wt. % | Mole % |
| --- | --- | --- |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

When transalkylation is desired, the transalkylating agent may be a polyalkyl aromatic hydrocarbon containing 2 or more alkyl groups that each may have from 2 to about 4 carbon atoms. For example, suitable polyalkyl aromatic hydrocarbons include di-, tri-, and tetra-alkyl aromatic hydrocarbons, such as diethylbenzene, triethylbenzene, diethylmethylbenzene (diethyltoluene), diisopropylbenzene, triisopropylbenzene, diisopropyltoluene, dibutylbenzene, and the like. Preferred polyalkyl aromatic hydrocarbons are the dialkyl benzenes. Particularly preferred polyalkyl aromatic hydrocarbons are diisopropylbenzene and diethylbenzene.

Reaction products which may be obtained from the process of the invention include ethylbenzene from the reaction of benzene with either ethylene or polyethylbenzenes, cumene from the reaction of benzene with propylene or polyisopropylbenzenes, ethyltoluene from the reaction of toluene with ethylene or polyethyltoluenes, cymenes from the reaction of toluene with propylene or polyisopropyltoluenes, and sec-butylbenzene from the reaction of benzene and n-butenes or polybutylbenzenes. The production of cumene from the alkylation of benzene with propylene or the transalkylation of benzene with diisopropylbenzene is an example of the production of a particular product.

The catalyst described herein comprises an oxide of a Group IVB metal, preferably zirconia or titania. This Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, Volume 4, pages 1727–1735 (1988), the entire disclosures of these publications are expressly incorporated herein by reference.

According to an optional modification of the Group IVB metal oxide described herein, a hydrogenation/dehydrogenation component is combined with the Group IV metal oxide. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The present catalyst may comprise one or more catalytic forms of one or more noble metals (i.e., Pt, Pd, Ir, Rh, Os or Ru). Combinations of catalytic forms of such noble or non-noble metals, such combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis.*, Volume 4, pages 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the isomerization of n-hexane.

Suitable sources of the Group IVB metal oxide, used for preparing the present catalyst, include compounds capable of generating such oxides, such as oxychlorides, chlorides, nitrates, etc., particularly of zirconium or titanium. Alkoxides of such metals may also be used as precursors or sources of the Group IVB metal oxide. Examples of such alkoxides include zirconium n-propoxide and titanium ipropoxide. Preferred sources of a Group IVB metal oxide are zirconium hydroxide, i.e., $Zr(OH)_4$, and hydrated zirconia. The expression, hydrated zirconia, is intended to connote materials comprising zirconium atoms covalently linked to other zirconium atoms via bridging oxygen atoms, i.e., Zr—O—Zr, further comprising available surface hydroxy groups. These available surface hydroxyl groups are believed to react with the source of an anion of a Group IVB metal, such as tungsten, to form the present acidic catalyst component. As suggested in the afornentioned article by K. Arata and M. Hino in *Proceedings 9th International Congress on Catalysis*, Volume 4, pages 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with a base solution prior to contact with a source of tungstate may be preferable. More particularly, refluxing hydrated zirconia in an $NH_4OH$ solution having a pH of greater than 7, e.g., about 9, was beneficial. Without wishing to be bound by any theory, it is theorized that the base-treated, hydrated zirconia is better because it has higher surface area. It is also theoretically possible that the base treatment alters surface hydroxyl groups on the hydrated zirconia, possibly in a manner which promotes a more desirable interaction with the source of tungstate later used.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperature may not be needed.

In the present catalyst, of the Group IVB oxides, zirconium oxide is preferred; and of the Group VIB anions, tungstate is preferred.

Qualitatively speaking, elemental analysis of the present catalyst will reveal the presence of Group IVB metal, Group VIB metal and oxygen. The amount of oxygen measured in such an analysis will depend on a number of factors, such as the valence state of the Group IVB and Group VIB metals, the form of the hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The acidic solid material prepared as above for use herein can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the acidic solid can be extruded before drying or partially dried and then extruded.

As mentioned previously, the catalyst described herein can optionally be used in intimate combination with a hydrogenating component such as tungsten, vanadium, molybdenum, rhenium, nickel, cobalt, chromium, manganese, or a noble metal such as platinum or palladium. Such component can be introduced in the catalyst composition by way of co-precipitation, exchanged into the composition, impregnated therein, or intimately physically admixed therewith. Such component can be impregnated in, or on, the acidic solid material such as, for example, by, in the case of platinum, treating the acidic solid material with a solution containing a platinum metal-containing ion. Thus, suitable platinum compounds for this purpose include chloroplatinic acid, platinum halides, and various compounds containing the platinum ammine complex.

Prior to its use in a catalytic process, the acidic solid material may be dehydrated, at least partially. This can be done by heating the solid material to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the material in a vacuum, but a longer time is required to obtain a sufficient amount of dehydration.

It may be desired to incorporate the acidic solid material with another material resistant to the temperatures and other conditions employed in organic conversion processes. Such other materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of another material in conjunction with the acidic solid material, i.e., combined therewith or present during synthesis of the acidic solid material, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. The acidic solid materials may be incorporated into naturally occurring clays, e.g., bentonite and kaolin, to improve the crush strength of the catalyst under commercial operating conditions. These other materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the acidic solid material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present acidic solid material also include inorganic oxides, notably alumina.

In addition to the foregoing materials, the acidic solid material can be composited with a porous matrix material such as silica-alumina, silica-magnesia, silica-zirconia, silica-thoria, silica-beryllia, silica-titania as well as ternary compositions such as silica-alumina-thoria, silica-aluminazirconia silica-alumina-magnesia and silica-magnesia-zirconia.

The relative proportions of finely divided acidic solid material and inorganic oxide matrix vary widely, with the crystal content ranging from about 1 to about 90 percent by weight and more usually, particularly when the composite is prepared in the form of beads, in the range of about 2 to about 80 weight percent of the composite.

The alkylation process of this invention is conducted such that the organic reactants, i.e., the alkylatable aromatic compound and the alkylating agent, are brought into contact with the catalyst composition in a suitable reaction zone such as, for example, in a flow reactor containing a fixed bed of the catalyst composition, under effective alkylation conditions. Such conditions include a temperature of from about 0° C. to about 500° C., and preferably between about 50° C. and about 250° C. The reaction generally takes place at pressures of from about 0.2 to about 250 atmospheres and preferably from about 1 to about 25 atmospheres. The molar ratio of alkylatable aromatic compound to alkylating agent can be from about 0.1:1 to about 50:1 and preferably can be from about 0.5:1 to about 5:1. Reaction is suitably accomplished utilizing a feed weight hourly space velocity (WHSV of between about 0.1 $hr^{-1}$ and about 500 $hr^{-1}$ and preferably from 0.5 $hr^{-1}$ to about 100 $hr^{-1}$ The latter WHSV is based upon the total weight of active catalyst (and binder if present).

The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

The alkylation process described herein can be carried out as a batch-type, semi-continuous or continuous operation utilizing a fixed or moving bed catalyst system. A particular embodiment entails use of a catalyst zone wherein the hydrocarbon charge is passed cocurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

When benzene is alkylated with ethylene to produce ethylbenzene, the alkylation reaction may be carried out in the liquid or vapor phase. Suitable liquid phase conditions can be selected by reference to the phase diagram for benzene. In the liquid phase, the reaction is carried out with the benzene feedstock in the liquid phase with the reaction conditions (temperature, pressure) appropriate to this end.

Liquid phase operation may be carried out at temperatures between 200° and 500° F. (about 93° to 260° C.), usually in the range of 400° to 500° F. (about 205° to 260° C.).

Pressures during the liquid phase alkylation step may be as high as about 3000 psig, (about 20875 kPa abs.) and generally will not exceed 1000 psig (about 7000 kPa). The reaction may be carried out in the absence of hydrogen and accordingly the prevailing pressures are those of the reactant species. In a high pressure liquid phase operation, the temperature may be from about 200° to 600° F. with the pressure in the range of about 400 to 800 psig. The space velocity may be from about 0.1 to 10 WHSV, based on the ethylene feed, although lower space velocities are preferred for the liquid phase reaction, for example, from about 0.1 to about 1 WHSV with values from about 0.2 to 0.5 WHSV (ethylene) being typical. The ratio of the benzene to the ethylene in the alkylation reactor may be from 1:1 to 30:1 molar normally about 5:1 to 20:1 and in most cases from about 5:1 to 10:1 molar.

When benzene is alkylated with propylene to produce cumene, the reaction may also take place under liquid phase conditions including a temperature of from about 10° C. to about 125° C., a pressure of from about 1 to about 30 atmospheres, and an aromatic hydrocarbon weight hourly space velocity (WHSV) of from 5 $hr^{-1}$ to about 50 $hr^{-1}$.

When transalkylation is the process conducted according to the invention, the molar ratio of aromatic hydrocarbon to polyalkyl aromatic hydrocarbon may range from about 1:1 to about 50:1, and preferably from about 2:1 to about 20:1. The reaction temperature may range from about 100° F. to 600° F., but it is preferably about 250° F. to 450° F. The reaction pressure may be sufficient to maintain at least a partial liquid phase, typically in the range of about 50 psig to 1000 psig, preferably 300 psig to 600 psig. The weight hourly space velocity will range from about 0.1 to 10.

When conducting either alkylation or transalkylation, various types of reactors can be used in the process of this invention. For example, the process can be carried out in batchwise fashion by adding the catalyst and aromatic feedstock to a stirred autoclave, heating to reaction temperature, and then slowly adding the olefinic or polyalkylaromatic feedstock. A heat transfer fluid can be circulated through the jacket of the autoclave, or a condenser can be provided, to remove the heat of reaction and maintain a constant temperature. Large scale industrial processes may employ a fixed-bed reactor operating in an upflow or downflow mode or a moving-bed reactor operating with concurrent or countercurrent catalyst and hydrocarbon flows. These reactors may contain a single catalyst bed or multiple beds and may be equipped for the interstage addition of olefins and interstage cooling. Interstage olefin addition and more nearly isothermal operation enhance product quality and catalyst life. A moving-bed reactor makes possible the continuous removal of spent catalyst for regeneration and replacement by fresh or regenerated catalysts.

In a particular embodiment of the present invention, the alkylation process is carried out with addition of olefin in at least two stages. Preferably, there will be two or more catalyst beds or reactors in series, wherein at least a portion of the olefin is added between the catalyst beds or reactors. Interstage cooling can be accomplished by the use of a cooling coil or heat exchanger. Alternatively, interstage cooling can be effected by staged addition of the aromatic feedstock in at least two stages. In this instance, at least a portion of the aromatic feedstock is added between the catalyst beds or reactors, in similar fashion to the staged addition of olefin described above. The staged addition of aromatic feedstock provides additional cooling to compensate for the heat of reaction.

In a fixed-bed reactor or moving-bed reactor, alkylation is completed in a relatively short reaction zone following the introduction of olefin. Ten to thirty percent of the reacting aromatic molecules may be alkylated more than once. Transalkylation is a slower reaction which occurs both in the alkylation zone and in the remainder of the catalyst bed. If transalkylation proceeds to equilibrium, better than 90 wt.% selectivity to monoalkylated product is generally achieved. Thus, transalkylation increases the yield of monoalkylated product by reacting the polyalkylated products with additional benzene.

The alkylation reactor effluent contains the excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the benzene distillation are further distilled to separate monoalkylated product from polyalkylated products and other heavies. In most cases, the recovered monoalkylated product should be very pure. For example, in the production of cumene, n-propylbenzene, butylbenzenes, ethylbenzene and alpha-methylstyrene all should be reduced to low (e.g., <100–300 ppm) levels since they are converted during the oxidation process to make phenol from cumene. Only small amounts of n-propylbenzene can be removed from cumene by distillation, and so the catalyst should make very low levels of this impurity. It is important to have a feedstock which is relatively free of ethylene and butylenes to avoid ethylbenzene and butylbenzenes in the cumene product; these contaminants can be removed by distillation, but to do so greatly increases the amount of required downstream fractionation.

Additional monoalkylated product may be produced by transalkylation. The polyalkylated products may be recycled to the alkylation reactor to undergo transalkylation or they may be reacted with additional aromatic feed in a separate reactor. It may be preferred to blend the bottoms from the distillation of monoalkylated product with a stoichiometric excess of the aromatic feed, and react the mixture in a separate reactor over a suitable transalkylation catalyst. The transalkylation catalyst may be a catalyst comprising the present acidic solid material and/or a zeolite such as MCM-49 or those materials designated MCM-22, PSH-3, SSZ-25, zeolite X, zeolite Y, or zeolite beta. The effluent from the transalkylation reactor may be blended with alkylation reactor effluent and the combined stream distilled. A bleed may be taken from the polyalkyated product stream to remove unreactive heavies from the loop or the polyalkyated product stream may be distilled to remove heavies prior to transalkylation.

EXAMPLE 1

This Example describes the preparation of a tungstate modified zirconia catalyst. One part by weight of zirconyl chloride, $ZrOCl_2 \cdot 8H_2O$, was added to 3 parts by weight of a 10M $NH_4OH$ solution. The resulting slurry, $Zr(OH)_4$, was filtered and washed with 5 parts of distilled deionized water, then air dried at 140° C. for 8 hours. Approximately 4.2 parts by weight of the resulting $Zr(OH)_4$ were impregnated via incipient wetness with 6.3 parts of an aqueous solution containing 1 part of ammonium metatungstate, $(NH_4)_6H_2W_{12}O_{40}$. The resulting material was dried for 2 hours at 120° C. and then calcined at 800° C. in flowing air for 2 hours. The sample was pretreated at 350° C. for 15 hours under flowing hydrogen prior to catalytic testing. This sample had a calculated mole ratio of $ZrO_2/WO_3$ of 6.5.

The tungstate-modified zirconia material of Example 1 is referred to hereinafter as $WO_x/ZrO_2$.

In the Examples which follow, experiments are described, wherein $WO_x/ZrO_2$ (13–30 mesh, no binder) was evaluated using a down flow, three-zone isothermal fixed-bed unit. Four grams of catalyst was diluted to ~20 cc with 20–40 mesh vycor chips to make up the active bed. The experiments were conducted under liquid phase conditions. Ethylbenzene synthesis from benzene and ethylene was used to demonstrate alkylation; whereas cumene synthesis from benzene and diisopropylbenzene (DIPB) was used to demonstrate transalkylation.

EXAMPLE 2

Liquid phase ethylbenzene (EB) synthesis was conducted at psig, 5.5 benzene/$C_2$=molar ratio, 0.55 $C_2$=WHSV (based on total catalyst), and 140°–220° C. Offgases were analyzed on a Carle refinery gas analyzer and liquid products were analyzed on a Varian 3700 GC. Ethylene conversion was determined by measuring unreacted $C_2$=offgas relative to feed $C_2$=. Total material balances were 100±2%. The performance of $WO_x/ZrO_2$ is summarized in Table 1.

TABLE 1

| Ethylbenzene Synthesis from Benzene and Ethylene (Alkylation) | |
|---|---|
| Catalyst | $WO_x/ZrO_2$ |
| Temp, °C. | 140 |
| $C_2$= conv. (%) | 97.1 |
| Product distr. (mol %) | |
| EB | 86.5 |
| DEB | 10.9 |
| TEB | 1.4 |
| Σ | 98.8 |
| xylenes | 0.00 |
| n-$C_3$—Bz+ cumene | 0.00 |
| sec-$C_3$—Bz | 0.45 |
| other $C_9$+ aromatics | 0.75 |
| Σ (by-products) | 1.20 |

The data show that $WO_x/ZrO_2$ is highly active and selective for liquid phase ethylbenzene synthesis from benzene and ethylene.

EXAMPLE 3

Liquid phase cumene synthesis was conducted at 500 psig, 5 benzene/DIPB molar ratio, 4 total LHSV (based on binder-free catalyst), and 180°–220° C. Liquid products were analyzed on the Varian 3700 GC. Total material balances were 100±2%. The performance of $WO_x/ZrO_2$ is summarized in Table 2.

TABLE 2

| Cumene Synthesis from Benzene and DIPB (Transalkylation) | |
|---|---|
| Catalyst | $WO_x/ZrO_2$ |
| Temp, °C. | 180 |
| DIPB conv. (%) | 72.4 |
| Benzene conv. (%) | 15.7 |
| Product distr. (wt. %) | |
| $C_3/C_3$= | 0.14 |
| Toluene | 0.00 |
| EB | 0.13 |
| Xylenes | 0.00 |
| Cumene | 98.86 |
| n-$C_3$—Bz | 0.09 |
| Polyisopropyl-benzene | 0.79 |
| Cumene/n-$C_3$—Bz | 1111 |

The data show that $WO_x/ZrO_2$ is also active and selective for liquid phase cumene synthesis from benzene and diisopropylbenzene.

What is claimed is:

1. A process for preparing short chain alkyl aromatic compounds, said process comprising contacting at least one alkylatable aromatic compound with at least one transalkylating agent possessing alkylating aliphatic groups having from 1 to 5 carbon atoms under sufficient reaction conditions and in the presence of a catalyst to provide an alkylated aromatic product possessing at least one alkyl group derived from said transalkylating agent, said catalyst comprising an acidic solid which is a Group IVB metal oxide modified with an acidity increasing amount of an oxyanion of a Group VIB metal.

2. The process of claim 1 wherein said Group IVB metal is zirconium and said Group VIB metal is tungsten.

3. The process of claim 1 wherein said catalyst comprises a matrix material.

4. The process of claim 3 wherein said matrix material comprises alumina, silica, or mixture thereof.

5. The process of claim 3 wherein the catalyst is provided in the form of extrudate, beads, or fluidizable microspheres.

6. The process of claim 1 wherein benzene is transalkylated with polyisopropylbenzene under liquid phase conditions to produce cumene.

7. The process of claim 1 wherein the alkylation reaction conditions include a temperature of from about 0° C. to about 500° C., a pressure of from about 0.2 to about 250 atmospheres, a WHSV of from about 0.1 to 500 hr$^{-1}$ and an alkylatable aromatic compound to transalkylating agent mole ratio of from about 0:1:1 to 50:1.

8. The process of claim 6 wherein the reaction conditions include a temperature of from about 10° C. to 125° C., a pressure of from about 1 to about 30 atmospheres, and a WHSV of from about 5 to about 50 hr$^-$.

9. The process of claim 2 wherein said acidic solid is prepared by impregnating zirconium hydroxide or hydrated zirconia with an aqueous solution containing tungstate anions followed by calcination at a temperature of from about 700° C. to about 850° C.

10. The process of claim 1 wherein the reaction conditions include a temperature of from about 100° to about 600° F., a pressure of from about 50 psig to about 1000 psig, and a WHSV of from about 0.1 to about 10.

11. The process of claim 1 wherein said alkylated aromatic product is ethylbenzene or cumene, said ethylbenzene being produced from the reaction of benzene with polyethylbenzenes, and said cumene being produced from the reaction of benzene with polyisopropybenzenes.

12. The process of claim 1, wherein said contacting is at a temperature in the range of from about 50° to about 250° C.

13. The process of claim 1, wherein said contacting is at a temperature in the range of from about 140° to about 220° C.

14. A process for preparing short chain alkyl aromatic compounds, said process comprising contacting at least one alkylatable aromatic compound with at least one transalkylating agent possessing alkylating aliphatic group having from 1 to 5 carbon atoms at a temperature in the range of from about 0° to about 220° C. and in the presence of a catalyst to provide an alkylated aromatic product possessing at least one alkyl group derived from said transalkylating agent, said catalyst comprising an acidic solid comprising a Group IVB metal oxide modified with an acidity increasing amount of an oxyanion of a Group VIB metal.

\* \* \* \* \*